United States Patent [19]

Dunbar et al.

[11] 4,080,497

[45] Mar. 21, 1978

[54] AMINECARBOTRITHIOATES AND PREPARATION

[75] Inventors: Joseph E. Dunbar; Joan H. Rogers, both of Midland, Mich.

[73] Assignee: The Dow Chemical Company, Midland, Mich.

[21] Appl. No.: 409,574

[22] Filed: Oct. 25, 1973

Related U.S. Application Data

[60] Division of Ser. No. 166,258, Jul. 26, 1971, Pat. No. 3,810,890, which is a continuation-in-part of Ser. No. 682,511, Nov. 13, 1967, abandoned.

[51] Int. Cl.$^2$ ............................................ C07D 265/30
[52] U.S. Cl. ................................. 544/85; 260/293.63; 260/293.85; 260/453 RZ; 424/298; 544/106
[58] Field of Search ........ 260/453 R, 455 A, 247.1 T, 260/293.85, 246 B; 424/300

[56] References Cited

U.S. PATENT DOCUMENTS

| | | | |
|---|---|---|---|
| 2,390,713 | 12/1945 | Hunt | 260/455 A |
| 2,792,394 | 5/1957 | Himel et al. | 260/455 A |

OTHER PUBLICATIONS

Pianka et al., "Studies in Fungitoxicity", etc.; (1966), J. Sci. Fd. Agric. 17, pp. 407–416, (1966).
Kulka "Hydrolipis and Hydrazinolysis etc.;", (1956), CA51, pp. 3481–3482, (1957).

*Primary Examiner*—Glennon H. Hollrah
*Attorney, Agent, or Firm*—Theodore Post; C. Kenneth Bjork

[57] ABSTRACT

A thiolsulfonate is reacted with an aminecarbodithioate salt to given an aminecarbotrithioate product. The products of this invention have biological activity, particularly in controlling microorganisms and other pests.

3 Claims, No Drawings

AMINECARBOTRITHIOATES AND PREPARATION

This application is a divisional application of U.S. Pat. application Ser. No. 166,258, filed July 26, 1971, now U.S. Pat. No. 3,810,890, issued May 14, 1974, which is a continuation-in-part of U.S. Pat. application Ser. No. 682,511, filed Nov. 13, 1967 now abandoned.

BACKGROUND OF THE INVENTION

This invention concerns a process for making aminecarbotrithioates by reaction between a thiosulfonate and an aminecarbodithioate salt, advantageously an alkali metal or ammonium salt. The reaction is carried out advantageously in the presence of one or more organic liquids in which either or both of the reactants is dissolved or suspended, and at a temperature ranging between about 20° and about 150° C., if desired under an inert atmosphere, e.g., nitrogen. The invention also concerns certain novel aminecarbotrithioates. The aminecarbotrithioates have biological activity, particularly in controlling microorganisms and other pests.

SUMMARY OF THE INVENTION

The process of this invention is represented by the following equations:

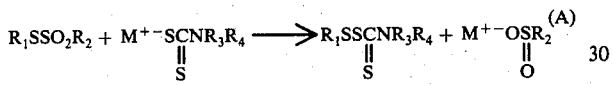

and

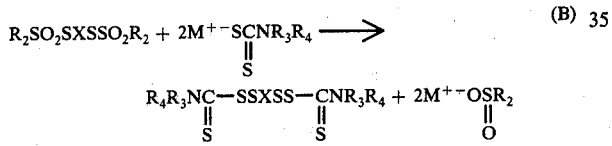

wherein $R_1$, $R_2$, $R_3$ and $R_4$ are defined below, to give the mono- and bis-aminocarbotrithioate products hereinafter shown.

The process of this invention gives rise to the following products, indicated by Formulas I–VI, as represented by the following equation:

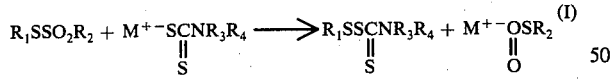

wherein $R_1$ represents alkenyl, loweralkyl- or halo-substituted alkenyl, 2-(loweralkoxy)ethyl, 2-(aryloxy)ethyl or propargyl, $R_2$ represents loweralkyl, aryl or loweralkyl or halo-substituted aryl and wherein $R_3$ and $R_4$ individually represent loweralkyl or hydrogen and together represent the remaining portion of a heterocyclic ring containing the nitrogen atom;

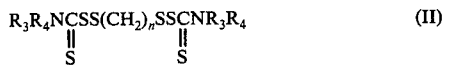

wherein $n$ represents an integer from 1, to 2, to 3, to 4, to 5, to 6, to 7, to 8, to 9, to 10, to 11, to 12, and wherein $R_3$ and $R_4$ individually represent loweralkyl or hydrogen and together represent the remaining portion of a heterocyclic ring containing the nitrogen atom;

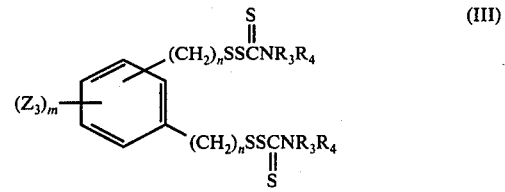

wherein $R_3$ and $R_4$ individually represent loweralkyl or hydrogen and together represent the remaining portion of a heterocyclic ring containing the nitrogen atom; wherein $n$ represents 0 or 1; wherein each $Z_3$ may be the same or different and represents loweralkyl, hydrogen, chloro, bromo, iodo, loweralkoxy, nitro or loweralkylthio; and wherein $m$ is 1, to 2, to 3, to 4, not more than two $Z_3$ groups of which are iodo or nitro;

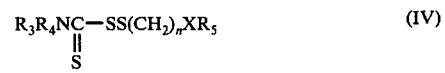

wherein $R_3$ and $R_4$ individually represent loweralkyl or hydrogen and together represent the remaining portion of a heterocyclic ring containing the nitrogen atom; $R_5$ represents loweralkyl, phenyl, loweralkylphenyl, halophenyl or loweralkoxyphenyl; $n$ is 1, to 2 and X is O or S;

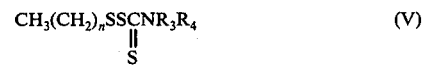

wherein $R_3$ and $R_4$ individually represent loweralkyl or hydrogen and together represent the remaining portion of a heterocyclic ring containing the nitrogen atom; and wherein $n$ is 10, to 11, to 12, to 13, to 14, to 15, to 16, to 17, to 18, to 19, to 20;

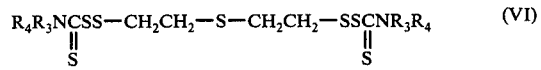

wherein $R_3$ and $R_4$ individually represent loweralkyl or hydrogen and together represent the remaining portion of a heterocyclic ring containing the nitrogen atom.

As used in the specification and claims, the terms "loweralkyl" and "loweralkoxy" designate alkyl and alkoxy groups having from 1 to 4 carbon atoms, such as, for example, methyl, ethyl, propyl and butyl; and methoxy, ethoxy, propoxy and butoxy, respectively.

DETAILED DESCRIPTION OF THE INVENTION

The process of this invention can be represented by the following equation for the monoaminecarbotrithioate Formula (I) compounds, the reaction involved being equally operable in the preparation of Formula (II)–(VI) compounds:

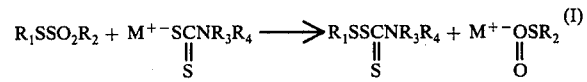

wherein
$M^+$ = alkali metal or ammonium cation
$R_2$ = loweralkyl, aryl or substituted aryl $R_1$ = alkenyl, substituted alkenyl, 2-(loweralkylthio)ethyl, 2-(arylthio)ethyl, 2-(loweralkoxy)ethyl, 2-(aryloxy)ethyl or propargyl and wherein $R_3$ and $R_4$ represent the remaining portion of a heterocyclic ring containing the nitrogen atom.

In the reaction, a single organic liquid or a mixture of two immiscible organic liquids or a mixture of a water immiscible liquid and water may be used as the reaction medium. For instance, the thiolsulfonate reactant may be dissolved in a water-immiscible solvent such as methylene chloride, chloroform, ethyl ether, benzene, toluene, xylene or commercial chlorinated solvents, and the carbodithioate salt may be dissolved in water. The two solutions are then mixed and vigorously agitated for a period of time from 5 minutes to 20 hours advantageously at a temperature ranging between 20° and 150° C. Again, both reactants may be completely soluble in a single organic solvent, or only one reactant may be completely soluble in the single organic liquid or neither reactant may be completely soluble in the single organic liquid. For another example, a solution of the thiolsulfonate in ethanol can be added to a suspension of the carbodithioate salt in ethanol, and the resulting mixture stirred at the required temperature to cause reaction. Solvents useful in single organic liquid systems include ethanol, methanol, isopropanol, acetone, methylethylketone, methylene chloride, chloroform, benzene, toluene, or xylene. When operating above the boiling point of the solvent system, a pressure vessel is advantageously used.

The amounts of the reactants to be employed in the reaction are not critical, some of the desired products being obtained when the reactants are employed in any proportions. In a preferred method, good yields are obtained when employing substantially stoichiometric proportions of the reactants. Bis(aminecarbotrithioates) are advantageously prepared by reacting two equivalents of an aminecarbodithioate, for example, sodium 4-morpholinecarbodithioate, with one equivalent of a thiolsulfonate, for example, 2,2'-bis(phenylsulfonylthio)diethyl sulfide to give thiodiethylene bis(morpholinecarbotrithioate). Up to 100 percent excess of either reactant is not deleterious, however.

Representative thiolsulfonates useful in the process of this invention include o-nitrophenyl benzenethiolsulfonate, dinitrophenyl benzenethiolsulfonate 2,3,3-tribromoallyl p-toluenethiolsulfonate, 2,3,3-tribromoallyl benzenethiolsulfonate, p-phenylene bis(methanethiolsulfonate), pentamethylene bis(methanethiolsulfonae) allyl p-toluenethiolsulfonate, $\alpha,\alpha'$-bis(methylsulfonylthio)-o-xylene, propargyl p-toluenethiolsulfonate, methyl methanethiolsulfonate, 2-methylbenzyl benzenethiolsulfonate, ethyl p-toluenethiolsulfonate, n-dodecyl p-toluenethiolsulfonate, benzyl p-toluenethiolsulfonate, 2-(methylthio)ethyl p-iodobenzenethiolsulfonate, 2-(methylthio)ethyl methanethiolsulfonate, 2,2'-bis(phenylsulfonylthio)diethyl sulfide, 2-(ethylthio)ethyl methanethiolsulfonate, 2-(phenoxy)ethyl benzenethiolsulfonate, 2-phenylallyl methanethiolsulfonate, 2,2'-bis(phenylsulfonylthio)diethyl sulfide and methylthiomethyl methanethiolsulfonate.

Representative aminocarbodithioate salts useful in the process of this invention include sodium, potassium, lithium and ammonium dithiocarbamate, dimethylaminecarbodithioate, diethylaminecarbodithioate, 1-piperidinecarbodithioate, and 4-morpholinecarbodithioate.

The novel compounds of this invention are particularly useful as pesticides for the control of various fungal and bacterial organisms and other pests such as *Bacillus subtilis, Staphylococcus aureus, Escherichia coli, Candida albicans, Trichophyton mentagrophytes, Venturia inaequalis, Piricularia oryzae, Aerobacter aerogenes, Salmonella typhosa, Candida pelliculosa, Pullularia pullulans, Rhizopus nigricans, Aspergillus terreus, Eimeria necatrix, Eimeria tenella* and *Daphnia*.

The following examples describe completely representative specific embodiments and the best modes contemplated by the inventors of carrying out their invention. Temperatures given are centigrade.

EXAMPLE 1 o-NITROPHENYL DIETHYLAMINECARBOTRITHIOATE

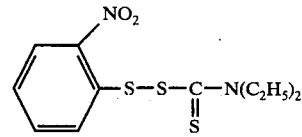

o-Nitrophenyl benzenethiolsulfonate (14.8 grams; 0.0500 mole) in 75 milliliters of methylene chloride and 8.7 grams (0.0510 mole) of sodium diethylaminecarbodithioate in 75 milliliters of water were combined and stirred vigorously for 18 hours at room temperature. The organic layer was separated, washed with water until free of water-soluble salts and dried over anhydrous magnesium sulfate. The solvent was removed by evaporation in vacuo, and the yellow, oily residue was crystallized (Norit) from 1:1 volumetric proportions of methylcyclohexane and benzene to give golden platelets, melting point 92°–93°. Recrystallization from the same methylcyclohexane-benzene mixture gave the pure o-nitrophenyl diethylaminecarbotrithioate, melting point 92.5°–93°.

Anal. Calcd. for $C_{11}H_{14}N_2O_2S_3$: C, 43.68; H, 4.67; N, 9.27; S, 31.80. Found: C, 43.69; H, 4.64; N, 8.93; S, 32.07.

EXAMPLE 2

2,3,3-TRIBROMOALLYL 1-PIPERIDINECARBOTRITHIOATE

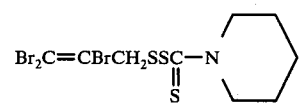

Sodium 1-piperidinecarbodithioate (6.7 grams; 0.033 mole) was added to a suspension of 15.0 grams (0.0330 mole) of 2,3,3-tribromoallyl p-toluenethiolsulfonate in 250 milliliters of methanol with stirring at room temperature. Dissolution of the reactants occurred immediately with concomitant formation of a yellow-orange color. The mixture was stirred vigorously at room temperature for 1.75 hours, and the product, 2,3,3-tribromoallyl 1-piperidinecarbotrithioate, was obtained as a light tan solid, melting point 84°–86°. Two recrystallizations from ethanol gave the pure substance as white crystals, melting point 84.5°–86.5°.

Anal. Calcd. for $C_9H_{12}Br_3NS_3$: C, 23.0; H, 2.57; Br, 51.0. Found: C, 23.0; H, 2.57; Br, 51.0.

EXAMPLE 3

2,3,3-TRIBROMOALLYL 4-MORPHOLINECARBOTRITHIOATE

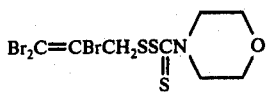

Sodium 4-morpholinecarbodithioate (18.5 grams; 0.100 mole) was added in one portion to a solution of 45.1 grams (0.100 mole) of 2,3,3-tribromoallyl benzenethiolsulfonate in 750 milliliters of methanol at room temperature with vigorous stirring. Stirring was continued for 20 minutes, and the cream-colored precipitate which had formed was collected on a filter, dried in vacuo and recrystallized from ethanol to give orange-brown crystals, melting point 112°-113.5°. A second recrystallization from ethanol gave the pure 2,3,3-tribromoallyl 4-morpholinecarbotrithioate as tan crystals, melting point 112.5°-114°.

Anal. Calcd. for $C_8H_{10}Br_3NOS_3$: C, 20.4; H, 2.14; Br, 50.8. Found: C, 20.4; H, 2.37; Br, 50.7.

EXAMPLE 4

PENTAMETHYLENE BIS(4-MORPHOLINECARBOTRITHIOATE)

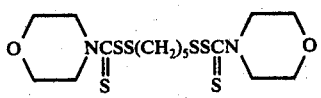

A solution of 3.7 grams (0.020 mole) of sodium 4-morpholinecarbodithioate in 25 milliliters of ethanol was added to a suspension of 2.9 grams (0.010 mole) of pentamethylene bis(methanethiolsulfonate) in 125 milliliters of ethanol. The reaction mixture was stirred at room temperature for 15 minutes, and the precipitated white crystalline product was collected on a filter and dried. Recrystallization from ethanol gave the pure pentamethylene bis(4-morpholinecarbotrithioate) as colorless crystals, melting point 83°-84.5°.

Anal. Calcd. for $C_{15}H_{26}N_2O_2S_6$: C, 39.27; H, 5.71; S, 41.93. Found: C, 39.3; H, 5.48; S, 41.49.

EXAMPLE 5

ALLYL 1-PIPERIDINECARBOTRITHIOATE

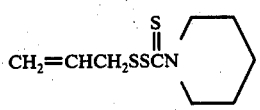

A mixture of 16.5 grams (0.0726 mole) of allyl p-toluenethiolsulfonate and 13.3 grams (0.0725 mole) of sodium 1-piperidinecarbodithioate in 200 milliliters of ethanol was heated at reflux temperature for one hour. The solvent was removed by evaporation in vacuo, leaving a mixture of crystalline material and oil. The mixture was slurried in ether and filtered to remove the insoluble by-product, sodium p-toluenesulfinate. The ether was removed by evaporation in vacuo to give the crude product as an amber oil. The material was chromatographed on an acid-washed activated alumina column, using 1:1 benzene-petroleum ether (boiling point 60°-70°). The pure allyl 1-piperidinecarbotrithioate was obtained as a yellow oil, $n_D^{25}$ 1.6339.

Anal. Calcd. for $C_9H_{15}NS_3$: C, 46.31; H, 6.48; N, 6.00; S, 41.21. Found: C, 46.2; H, 6.56; N, 5.92; S, 41.70.

EXAMPLE 6 o-XYLYLENE BIS(4-MORPHOLINECARBOTRITHIOATE)

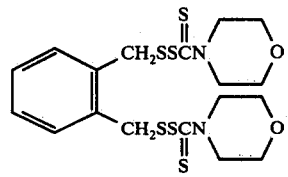

A mixture of 10.0 grams (0.0306 mole) of $\alpha,\alpha'$-bis(methylsulfonylthio)-o-xylene and 11.3 grams of (0.0612 mole) of sodium 4-morpholinecarbodithioate in 300 milliliters of ethanol was stirred at room temperature for 30 minutes. The precipitate which formed was collected by filtration and stirred with hot ethanol. The ethanol-insoluble crude product was collected on a filter, air-dried and recrystallized from acetonitrile to give the pure o-xylylene bis(4-morpholinecarbotrithioate) as ivory-colored crystals, melting point 174°-175°.

Anal. Calcd. for $C_{18}H_{24}N_2O_2S_6$: C, 43.87; H, 4.91; N, 5.69. Found: C, 43.7; H, 4.70; N, 5.54.

EXAMPLE 7

PROPARGYL 4-MORPHOLINECARBOTRITHIOATE

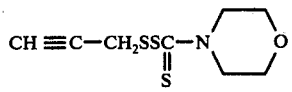

A mixture of 9.0 grams (0.040 mole) of propargyl p-toluenethiolsulfonate and 7.4 grams (0.040 mole) of sodium 4-morpholinecarbodithioate in 300 milliliters of ethyl ether was stirred at room temperature for 17 hours. During this period of time the by-product sodium p-toluenesulfinate had precipitated as white crystals and was removed by filtration. The solvent was removed from the filtrate by evaporation in vacuo, leaving an oily, red solid. The substance was dissolved in a minimum amount of benzene and precipitated by the addition of petroleum ether (boiling point 60°-70°) to give a yellow, crystalline, crude product. Recrystallization from isopropanol gave the pure propargyl 4-morpholinecarbotrithioate as pale yellow crystals, melting point 77°-78°.

Anal. Calcd. for $C_8H_{11}NOS_3$: H, 41.2; H, 4.75; N, 6.00. Found: C, 41.4; H, 5.12; N, 6.11.

EXAMPLE 8

METHYL DIETHYLAMINECARBOTRITHIOATE

A mixture of 41.0 grams (0.325 mole) of methyl methanethiolsulfonate, 116.8 grams (0.0682 mole) of sodium diethylaminecarbodithioate, 400 milliliters of methylene chloride and 25 milliliters of water was stirred vigorously at room temperature for 48 hours. The methylene chloride layer was separated, washed with water and dried over anhydrous magnesium sulfate. Removal of the solvent by evaporation in vacuo gave the methyl diethylaminecarbotrithioate as a yellow oil, $n_D^{25}$ 1.6111. The oil was crystallized at low temperature from a solution of ethyl ether and petroleum ether (boiling point 60°-70°) to give a low melting yellow solid, which was quickly collected on a sintered glass Buechner funnel and dried in vacuo as a liquid in an Abderhalden drying pistol. The purified product, methyl diethylaminecarbotrithioate, was obtained as a yellow oil, $n_D^{25}$ 1.6118.

Anal. Calcd. for $C_6H_{13}NS_3$: C, 36.9; H, 6.71; S, 49.23. Found: C, 37.5; H, 6.91; S, 49.57.

EXAMPLE 9 o-NITROPHENYL 4-MORPHOLINECARBOTRITHIOATE

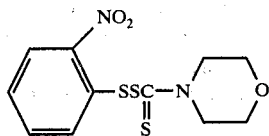

A solution of 16.0 grams (0.0865 mole) of sodium 4-morpholinecarbodithioate in 50 milliliters of water was added to a solution of 25.1 grams (0.0850 mole) of o-nitrophenyl benzenethiolsulfonate in 250 milliliters of methylene chloride, and the reaction mixture was stirred vigorously at room temperature for four hours. After standing at room temperature for an additional 13 hours, the methylene chloride layer was separated, washed with water and dried over anhydrous magnesium sulfate. The solvent was then removed by evaporation in vacuo, leaving the crude product as bright yellow crystals. Two recrystallizations from ethanol gave the pure o-nitrophenyl 4-morpholinecarbotrithioate as yellow crystals, melting point 158°-160°.

Anal. Calcd. for $C_{11}H_{12}N_2O_3S_3$: C, 41.75; H, 3.82; N, 8.86. Found: C, 41.7; H, 3.87; N, 8.68.

EXAMPLE 10 o-NITROPHENYL 1-PIPERIDINECARBOTRITHIOATE

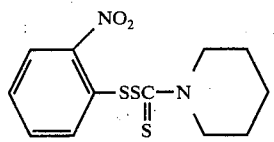

A solution of 20.1 grams (0.110 mole) of sodium 1-piperidinecarbodithioate in 50 milliliters of water was added to a solution of 29.5 grams (0.100 mole) of o-nitrophenyl benzenethiolsulfonate in 200 milliliters of methylene chloride, and the reaction mixture was stirred at room temperature for 30 hours. The methylene chloride layer was separated, washed with water and dried over anhydrous magnesium sulfate. The solvent was removed by evaporation in vacuo, leaving the bright yellow, crystalline, crude product. Two recrystallizations from acetonitrile gave the pure o-nitrophenyl 1-piperidinecarbotrithioate as bright yellow crystals, melting point 149.5°-151.5°.

Anal. Calcd. for $C_{12}H_{14}N_2O_2S_3$: C, 45.84; H, 4.49; N, 8.91. Found: C, 45.8; H, 4.51; N, 8.84.

EXAMPLE 11

2-METHYLBENZYL DIMETHYLAMINECARBOTRITHIOATE

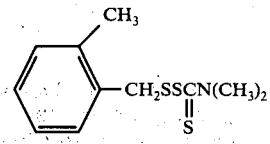

A mixture of 27.8 grams (0.100 mole) of 2-methylbenzyl benzenethiolsulfonate and 19.7 grams (0.110 mole) of sodium dimethylaminecarbodithioate dihydrate in 300 milliliters of methanol was stirred at room temperature for 20 hours. The white solid which had formed was collected on a filter and dried. The crude substance was twice recrystallized from ethanol to give the pure 2-methylbenzyl dimethylaminecarbotrithioate as colorless crystals, melting point 83°-85°.

Anal. Calcd. for $C_{11}H_{15}NS_3$: C, 51.32; H, 5.87; N, 5.44. Found: C, 51.3; H, 6.01; N, 5.33.

EXAMPLE 12

ETHYL DIMETHYLAMINECARBOTRITHIOATE

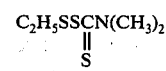

A mixture of 18.0 grams (0.0832 mole) of ethyl p-toluenethiolsulfonate and 16.4 grams (0.0915 mole) of sodium dimethylaminocarbodithioate dihydrate in 250 milliliters of methanol was stirred at room temperature for two hours. The solvent was then removed by evaporation in vacuo, leaving an oily residue which was slurried in ether and filtered to remove the insoluble by-product, sodium p-toluenesulfinate. The ether filtrate was dried over anhydrous magnesium sulfate and evaporated to dryness, leaving the crude product as a pale green oil. Treatment of a solution of the crude product in methylene chloride with activated alumina, with subsequent filtration and evaporation of the solvent, gave the ethyl dimethylaminecarbotrithioate as a pale yellow oil, $n_D^{25}$ 1.6205. (Lit. $n_D^{25}$ 1.6278; A. A. Watson, J. Chem. Soc., 1964, 2100).

EXAMPLE 13 n-DODECYL DIMETHYLAMINECARBOTRITHIOATE

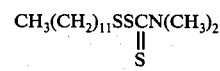

A solution of 13.8 grams (0.0772 mole) of sodium dimethylaminecarbodithioate dihydrate in 150 milliliters of methanol was slowly added with stirring to a suspension of 25.0 grams (0.0702 mole) of n-dodecyl p-toluenethiolsulfonate in 150 milliliters of methanol. The reaction mixture was stirred at room temperature for 16 hours during which time the product precipitated. The white, crystalline precipitate was collected on a filter and recrystallized from ethanol to give the pure n-dodecyl dimethylaminecarbotrithioate as colorless crystals, melting point 48°–50°.

Anal. Calcd. for $C_{15}H_{31}NS_3$: C, 56.02; H, 9.72; N, 4.36. Found: C, 56.3; H, 9.98; N, 4.37.

EXAMPLE 14

BENZYL DIMETHYLAMINECARBOTRITHIOATE

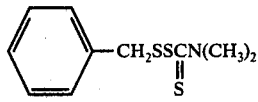

A solution of 17.8 grams (0.0640 mole) of benzyl p-toluenethiolsulfonate in 150 milliliters of methanol was added to a stirred suspension of 12.6 grams (0.0700 mole) of sodium dimethylaminecarbodithioate dihydrate in 150 milliliters of methanol, and the mixture was stirred at room temperature for 18 hours. During the reaction period the crude product precipitated as white crystals and was collected on a filter. The filtrate was evaporated to dryness, and the residue was extracted with methylene chloride, leaving the by-product, sodium p-toluenesulfinate, undissolved. The methylene chloride extract was concentrated to give a further amount of the crude benzyl dimethylaminecarbotrithioate, which was combined with the first amount. Recrystallization from ethanol (Norit) gave the pure benzyl dimethylaminecarbotrithioate as long, colorless needles, melting point 86.5°–87°. (Lit. melting point 85°, U.S. Pat. No. 3,232,974, Imperial Chemical Industries, Ltd.).

Anal. Calcd. for $C_{10}H_{13}NS_3$: C, 49.34; H, 5.38; N, 5.76. Found: C, 49.35; H, 5.44; N, 5.40.

EXAMPLE 15

2-METHYLBENZYL 1-PIPERIDINECARBOTRITHIOATE

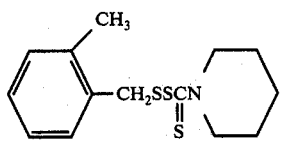

A solution of 24.1 grams (0.110 mole) of sodium 1-piperidinecarbodithioate in 200 milliliters of methanol was added with stirring to a suspension of 27.8 grams (0.100 mole) of 2-methylbenzyl benzenethiolsulfonate in 100 milliliters of methanol. The formation of a white precipitate was observed immediately. The reaction mixture was allowed to stand at room temperature for 20 hours and was then filtered to collect the white, crystalline, crude product. Recrystallization from isopropanol gave the pure 2-methylbenzyl 1-piperidinecarbotrithioate as colorless crystals, melting point 103°–105°.

Anal. Calcd. for $C_{14}H_{19}NS_3$: C, 56.56; H, 6.44; N, 4.71. Found: C, 56.6; H, 6.55; N, 4.87.

EXAMPLE 16

2-(METHYLTHIO)ETHYL DIMETHYLAMINECARBOTRITHIOATE

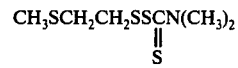

A solution of 16.1 grams (0.0431 mole) of 2-(methylthio)ethyl p-iodobenzenethiolsulfonate in 75 milliliters of methanol was added with stirring to a solution of 8.5 grams (0.047 mole) of sodium dimethylaminecarbodithioate dihydrate in 75 millilters of methanol, and the reaction mixture was stirred for 15 hours at room temperature. The solvent was removed by evaporation in vacuo, leaving a residue of white solid. The residue was extracted with methylene chloride and the sodium p-iodobenzenesulfinate by-product removed by filtration. The filtrate was concentrated to give the crude product as a white solid, which was collected of a filter and recrystallized from methanol to give the pure 2-(methylthio)ethyl dimethylaminecarbotrithioate as colorless needles, melting point 36°–37°.

Anal. Calcd. for $C_6H_{13}NS_4$: C, 31.68; H, 5.76; N, 6.16. Found: C, 31.7; H, 6.00; N, 5.93.

EXAMPLE 17

2-(METHYLTHIO)ETHYL DIMETHYLAMINECARBOTRITHIOATE

A solution of 10.6 grams (0.0592 mole) of sodium dimethylaminecarbodithioate dihydrate in 100 milliliters of methanol was purged of air by a stream of nitrogen. 2-(Methylthio)ethyl methanethiolsulfonate (10.0 grams., 0.0537 mole) in 100 milliliters of methanol was then added slowly with stirring at room temperature. After the mixture had been stirred under nitrogen at room temperature overnight the solvent was removed by evaporation in vacuo to leave an oily residue which, when shaken with methylene chloride, left a water miscible layer which was separated from the organic phase and discarded. The methylene chloride solution was concentrated to give white crystals, melting point 35°–36°, with some remaining solid not completely melting until a temperature of 105° was reached. A lengthy fractional crystallization procedure, using methanol as a recrystallizing solvent, gave the pure product as colorless needles, melting point 36°–37°. A mixture of this substance and a sample of the authentic substance gave no depression of melting point.

EXAMPLE 18

2-(METHYLTHIO)ETHYL 4-MORPHOLINECARBOTRITHIOATE

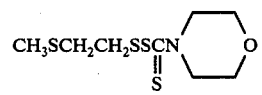

A solution of 21.8 grams (0.118 mole) of sodium 4-morpholinecarbodithioate in 150 milliliters of methanol was added slowly at room temperature to a stirred solution of 20.0 grams (0.107 mole) of 2-(methylthio)ethyl methanethiolsulfonate in 150 milliliters of methanol. Stirring was continued for 15 hours, and the solvent was then removed by evaporation in vacuo. The yellow oily residue was shaken with water and the mixture extracted with methylene chloride. After the extract was dried over anhydrous magnesium sulfate the methylene chloride was removed by evaporation, leaving 27.0 grams of a turbid, yellow oil $n_D^{25}$ 1.6473. Residual solvent was removed by vacuum distillation, leaving 25.0 grams of yellow oil which was dissolved in methylene chloride, the solution treated with activated charcoal and filtered. Upon removing the methylene chloride in vacuo, the residue was found to consist of a clear, yellow oil, $n_D^{25}$ 1.6445.

Anal. Calcd. for $C_8H_{15}NOS_4$: C, 35.66; H, 5.61; N, 5.20. Found: C, 35.4; H, 5.48; N, 5.43.

EXAMPLE 19 n-DODECYL 1-PIPERIDINECARBOTRITHIOATE

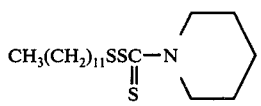

A solution of 9.7 grams (0.0440 mole) of sodium 1-piperidinecarbodithioate in 150 milliliters of methanol was added with stirring to a suspension of 14.3 grams (0.0401 mole) of n-dodecyl p-toluenethiolsulfonate in 150 milliliters of methanol at room temperature. A thick, white precipitate formed almost immediately. The reaction mixture was allowed to stand at room temperature for 16.5 hours. The mixture was then collected on a filter and dried. Two recrystallizations from ethanol gave the pure product as white crystals, melting point 47.5°–49.5°.

Anal. Calcd. for $C_{18}H_{35}NS_3$: C, 59.78; H, 9.75; N, 3.88. Found: C, 59.8; H, 10.04; N, 4.14.

EXAMPLE 20

THIODIETHYLENE BIS(4-MORPHOLINECARBOTRITHIOATE)

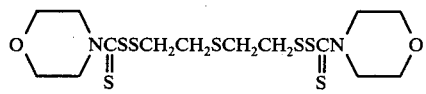

Sodium 4-morpholinecarbodithioate (18.5 grams; 0.100 mole) was added to a warm, stirred solution of 21.7 grams (0.0500 mole) of 2,2'-bis(phenylsulfonylthio)diethyl sulfide with the immediate formation of a voluminous, white precipitate. The reaction mixture was heated under reflux with stirring for 15 minutes and the white, crystalline product collected on a filter and washed with water to remove the sodium benzenesulfinate by-product. The crude product was recrystallized from methanol to give a very pale yellow solid, melting point 116.5°–117.5°. A second recrystallization from methanol gave a pure product as pale yellow crystals, melting point 117°–117.5°.

Anal. Calcd. for $C_{14}H_{24}N_2O_2S_7$: C, 35.27; H, 5.07; N, 5.88. Found: C, 35.2; H, 4.97; N, 5.79.

EXAMPLE 21

2-(METHYLTHIO)ETHYL DIETHYLAMINECARBOTRITHIOATE

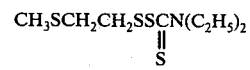

To a stirred solution of 27.2 grams (0.121 mole) of sodium diethylaminecarbodithioate trihydrate in 100 milliliters of methanol was slowly added a solution of 15.0 grams (0.0806 mole) of 2-(methylthio)ethyl methanethiolsulfonate in 100 milliliters of methanol under nitrogen. The reaction mixture was then stirred at room temperature under nitrogen for 18 hours. Evaporation of the solvent left an oil which was washed with water. The water washings were combined and washed with methylene chloride. The oil portion was added to the methylene chloride extract and the resulting solution dried over anhydrous magnesium sulfate. The solution was then treated with decolorizing charcoal, filtered and concentrated in vacuo to give a clear, yellow oil, $n_D^{25}$ 1.6137.

Anal. Calcd. for $C_8H_{17}NS_4$: C, 37.57; H, 6.71; N, 5.48. Found: C, 38.0; N, 6.69; N, 5.40.

EXAMPLE 22

2-(ETHYLTHIO)ETHYL 4-MORPHOLINECARBOTRITHIOATE

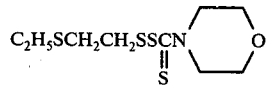

A mixture of 11.0 grams (0.055 mole) of 2-(ethylthio)ethyl methanethiolsulfonate and 12.2 grams (0.066 mole) of sodium 4-morpholinecarbodithioate in 300 milliliters of methanol was stirred at room temperature for 18 hours. The solvent was removed in vacuo, leaving an oily, crystalline mass which was stirred in ether and filtered to remove the insoluble by-product. The filtrate was dried over anhydrous magnesium sulfate and was evaporated to dryness to give a yellow oil. The oil was crystallized by cooling in a dry-ice-methylene chloride bath and recrystallized from methanol. Two recrystallizations from isopropanol gave the pure substance as colorless crystals, melting point 31°–32.5°.

Anal. Calcd. for $C_9H_{17}NOS_4$: C, 38.13; H, 6.05; N, 4.95. Found: C, 38.0; H, 5.85; N, 4.96.

EXAMPLE 23

2-PHENOXYETHYL 4-MORPHOLINECARBOTRITHIOATE

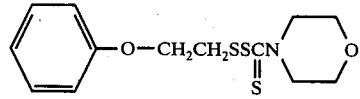

A solution of 15.1 grams (0.0816 mole) of sodium 4-morpholinecarbodithioate in 150 milliliters of methanol was added with stirring to a suspension of 20.0 grams (0.0680 mole) of 2-(phenoxy)ethyl benzenethiolsulfonate in 150 milliliters of methanol. A thick, white precipitate began forming immediately. The reaction mixture was stirred at room temperature for 19 hours, and the precipitate was collected on a filter. Recrystallization of product from methanol gave the pure substance as colorless crystals, melting point 89°–91°.

Anal. Calcd. for $C_{13}H_{17}NO_2S_3$: C, 49.49; H, 5.43; N, 4.44. Found: C, 49.2; H, 5.50; N, 4.47.

EXAMPLE 24

2-PHENYLALLYL 4-MORPHOLINECARBOTRITHIOATE

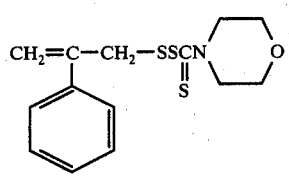

A solution of 16.7 grams (0.0732 mole) of 2-phenylallyl methanethiolsulfonate and 16.3 grams (0.0878 mole) of sodium 4-morpholinecarbodithioate in 300 milliliters of methanol was stirred at room temperature for 28 hours. The solvent was removed in vacuo, leaving a yellow residue which was stirred in ether and filtered to remove the insoluble by-product, sodium methanesulfinate. The ether filtrate was dried over anhydrous magnesium sulfate and evaporated to dryness to obtain a yellow, viscous oil. Trituration with a small amount of cold ether gave the crude, crystalline product which was collected on a filter. Recrystallization of product from ethanol gave the pure substance as colorless crystals, melting point 69.5°–71°.

Anal. Calcd. for $C_{14}H_{17}NOS_3$: C, 53.98; H, 5.51, N, 4.50. Found: C, 54.0; H, 5.38; N, 4.31.

EXAMPLE 25

THIODIETHYLENE BIS(DIMETHYLAMINECARBOTRITHIOATE)

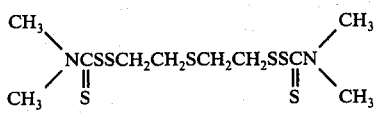

Sodium dimethylaminecarbodithioate dihydrate (14.2 grams; 0.0792 mole) was added to a warm, stirred solution of 17.2 grams (0.0396 mole) of 2,2'-bis(phenylsulfonylthio)diethyl sulfide in 700 milliliters of methanol. The mixture was heated under reflux with stirring for one hour, after which time the methanol was removed by evaporation in vacuo. The solid residue was extracted with water at room temperature to remove the by-product, sodium benzenesulfinate, collected on a filter and dried in vacuo over calcium chloride. Two recrystallizations from ethyl acetate gave the pure substance as colorless crystals, melting point 105°–105.5°.

Anal. Calcd. for $C_{10}H_{20}N_2S_7$: C, 30.58; H, 5.13; N, 7.14. Found: C, 30.6; H, 5.10; N, 7.25.

EXAMPLE 26

METHYLTHIOMETHYL 4-MORPHOLINECARBOTRITHIOATE

A solution of 13.0 grams (0.0700 mole) of sodium 4-morpholinecarbodithioate in 125 milliliters of methanol was added to a solution of 10.0 grams (0.0580 mole) of methylthiomethyl methanethiolsulfonate in 125 milliliters of methanol, and the reaction mixture was stirred at room temperature for 16 hours. The white precipitate, which had formed during the reaction period, was collected on a filter and recrystallized from methanol to give the pure methylthiomethyl 4-morpholine carbotrithioate as pale yellow crystals, melting point 55°–57°.

Anal. Calcd. for $C_7H_{13}NOS_4$: C, 32.88; H, 5.13; N, 5.49. Found: C, 33.1; H, 4.81; N, 5.41.

The compounds of the present invention are variously useful as pesticides for the control of various bacteria, fungi, mollusks, crustaceans, insects and terrestial plants. For such use, the unmodified compounds can be employed. Alternatively, the compounds can be dispersed on an inert finely divided solid and the resulting preparation employed as a dust. Also, such compounds or dust compositions containing said compounds can be dispersed in water with or without the aid of additional wetting agents and the resulting aqueous dispersions employed as sprays. In other procedures, the compounds can be employed as solutions in petroleum distillates or in other solvents or as constituents of oil-in-water or water-in-oil emulsions. Such liquid compositions can be employed as sprays, drenches or washes.

In representative operations, the compound of Example 2 gives good control of nymphal American cockroaches. In the test method, a paper cylindrical cage is provided, fitted on the bottom with a number 52 Whatman filter paper and on the top with retaining screen. Twenty-five nymphal cockroaches are inactivated with $CO_2$ and immersed in an aqueous dispersion of 1,000 parts per million by weight of the compound of Example 2 contained in the cage. The water is drawn off by suction through the filter paper. The nymphs are then fed with sugar water and left in the cage for three days, when a mortality count is made. Under such conditions, substantially complete control is attained. The same compound is separately dispersed in a series of melted nutrient agar samples to product a bacteriological culture medium containing 500 p.p.m. thereof by weight of ultimate medium. Each of these media is then poured into a separate Petri dish and allowed to solidify. The solidified agar surface in each Petri dish is separately inoculated with one of *Staphylococcus aureus, Bacillus subtilis, Aspergillus terreus, Candida pelliculosa, Pullularia pullulans* or *Salmonella typhosa*, the inoculation being carried out by mopping the agar surfaces with a swab from a 24-hour broth culture of the organism. After 72 hours incubation at 30° C., the agar surface of each Petri dish is examined for micro-organisms. In each of the series, the control is 100 percent. A control culture, to which none of the compound is added, shows vigorous growth.

The compound of Example 3 is similarly 100 percent effective against *Staphylococcus aureus* and *Bacillus subtilis* at a concentration of 500 p.p.m.

The compound of Example 5 is similarly effective against *Staphylococcus aureus, Candida albicans* and *Trichophyton mentagrophytes*, but at 100 p.p.m. concentration. This compound is also effective in controlling *Daphina* and *Carassius auratus* when 100 p.p.m. of compound is dispersed in water containing these organisms. *Piricularia oryzae* is controlled 100 percent by application of an aqueous dispersion containing 100 p.p.m. of compound. Amaranthus species is 100 percent controlled by application to the soil of 10 lb./acre of the compound applied in aqueous dispersion as a drench to soil containing viable seed of said species.

The compound of Example 7 is 100 percent effective against the American cockroach at a concentration of 1000 p.p.m. used in the form of an aqueous dispersion. An aqueous dispersion of 150 p.p.m., when sprayed on cucumber plants and potato plants, respectively, gives 100 percent control against *Erysiphe cichoracearum* and 95 percent control against *Phytophthora infestans*.

The compounds of Example 24 is similarly 100 percent effective against the American cockroach and against *Staphylococcus aureus* at 500 p.p.m. and 100 percent effective against *Candida albicans, Trichophyton mentagrophytes, Bacillus subtilis, Aspergillus terreus, Candida pelluculosa, Pullularia pullulans* and *Mycobacterium phlei*, all at a concentration of 100 p.p.m.

The following table shows effectiveness of other compounds at the stated concentrations, using tests as described above.

| Compound | Effective for 100% Control of: | Concentration |
| --- | --- | --- |
| Example 6 | Crabgrass | 4,000 p.p.m. |
| Example 16 | Daphnia | 2 p.p.m. |
| | Ram's horn snail | 2 p.p.m. |
| | Goldfish | 2 p.p.m. |
| | Cucumber powder mildew | 75 p.p.m. |
| Example 18 | Daphnia | 0.4 p.p.m. |
| | Goldfish | 2 p.p.m. |
| | Cucumber powdery mildew | 150 p.p.m. |
| | Apple scab fungus | 400 p.p.m. |
| | S. aureus | 100 p.p.m. |
| | E. Coli | 100 p.p.m. |
| | C. albicans | 100 p.p.m. |
| | T. mentagrophytes | 100 p.p.m. |
| | B. subtilis | 100 p.p.m. |
| | A. aerogenes | 100 p.p.m. |
| | A. terreus | 10 p.p.m. |

-continued

| Compound | Effective for 100% Control of: | Concentration |
| --- | --- | --- |
| Example 21 | C. pelliculosa | 100 p.p.m. |
| | P. pullulans | 100 p.p.m. |
| | S. typhosa | 100 p.p.m. |
| | E. Coli | 500 p.p.m. |
| | C. albicans | 100 p.p.m. |
| | T. mentagrophytes | 100 p.p.m. |
| | B. subtilis | 100 p.p.m. |
| | A. terreus | 100 p.p.m. |
| | C. pelliculosa | 100 p.p.m. |
| | P. pullulans | 100 p.p.m. |
| | S. typhosa | 100 p.p.m. |
| Example 22 | S. aureus | 500 p.p.m. |
| | C. albicans | 500 p.p.m. |
| | T. mentagrophytes | 100 p.p.m. |
| | B. subtilis | 100 p.p.m. |
| | A. terreus | 100 p.p.m. |
| | C. pelliculosa | 100 p.p.m. |
| | p. pullulans | 100 p.p.m. |
| | Bread mold fungus | 500 p.p.m. |
| Example 5 | S. aureus | 500 p.p.m. |
| | T. mentagrophytes | 500 p.p.m. |
| | B. subtilis | 500 p.p.m. |
| | Bean mildew | 100 p.p.m. |
| Example 19 | S. sureus | 100 p.p.m. |
| | T. mentagrophytes | 100 p.p.m. |
| | P. pullulans | 100 p.p.m. |
| | Ram's horn snail | 2 p.p.m. |
| Example 4 | Amaranthus spp. | 25 lb./acre |
| Example 25 | S. aureus | 100 p.p.m. |
| | C. albicans | 100 p.p.m. |
| | T. mentagrophytes | 100 p.p.m. |
| | B. subtilis | 100 p.p.m. |
| | A. terreus | 100 p.p.m. |
| | C. pelliculosa | 100 p.p.m. |

What is claimed is:

1. A compound corresponding to the formula $R_4R_3NC(=S)SS-CH_2CH_2-S-CH_2CH_2SSC(=S)NR_3R_4$ wherein $R_3$ and $R_4$ individually represent loweralkyl or hydrogen or together with the nitrogen atom represent a piperidino or a morpholino group.

2. The compound of claim 1 which is thiodiethylene bis(dimethylaminecarbotrithioate).

3. The compound of claim 1 which is thiodiethylene bis(4-morpholinecarbotrithioate).

* * * * *

UNITED STATES PATENT AND TRADEMARK OFFICE
CERTIFICATE OF CORRECTION

PATENT NO. : 4,080,497
DATED : March 21, 1978
INVENTOR(S) : Joseph E. Dunbar and Joan H. Rogers It is certified that error appears in the above-identified patent and that said Letters Patent are hereby corrected as shown below:

Title Page under "ABSTRACT", second line of paragraph, "given" should read -- give --;

Column 2, line 48 "loweralkyl" please correct quotation marks;

Column 2, between lines 60 and 65 "Equation" should read as follows:

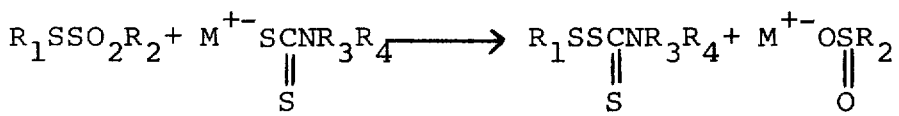

Column 3, line 47 "benzenethiolsulfonate 2,3,3-tri-" should read -- benzenethiolsulfonate, 2,3,3-tri- --;

Column 3, line 50 "(methanethiolsulfonae)" should read -- (methanethiolsulfonate) --;

Column 5, line 58 "(0.0725 mole)" should read -- (0.726 mole) --;

Column 6, line 19 "11.3 grams of" should read -- 11.3 grams--;

Column 10, line 14 "millilters" should read -- milliliters --;

Column 10, line 21 "of" should read -- on --;

UNITED STATES PATENT AND TRADEMARK OFFICE
CERTIFICATE OF CORRECTION

PATENT NO. : 4,080,497
DATED : March 21, 1978
INVENTOR(S) : Joseph E. Dunbar and Joan H. Rogers It is certified that error appears in the above-identified patent and that said Letters Patent are hereby corrected as shown below:

Column 14, line 33 "with retaining" should read
-- with a retaining --;

Column 14, line 65 "Daphina" should read -- Daphnia --;

Column 16, line 40 "moropholinecarbotrithioate)"
should read -- morpholinecarbotrithioate) --.

Signed and Sealed this

Tenth Day of October 1978

[SEAL]

Attest:

RUTH C. MASON
Attesting Officer

DONALD W. BANNER
Commissioner of Patents and Trademarks